United States Patent [19]

Robson

[11] 4,150,099

[45] Apr. 17, 1979

[54] SYNTHETIC HALLOYSITES

[75] Inventor: Harry E. Robson, Baton Rouge, La.

[73] Assignee: Exxon Research & Engineering Co., Florham Park, N.J.

[21] Appl. No.: 525,205

[22] Filed: Nov. 19, 1974

[51] Int. Cl.$^2$ ............................................. C01B 33/26
[52] U.S. Cl. ............................... 423/329; 252/455 R; 423/328
[58] Field of Search ............... 423/327, 328, 329, 330; 252/455 R, 455 Z; 208/120

[56] References Cited

U.S. PATENT DOCUMENTS 2,744,056  5/1956  Offutt et al. .......................... 208/120

OTHER PUBLICATIONS

Ross et al., "Halloysite and Allophane", Professional Paper 185-G, 1934, U.S. Dept. of the Interior, pp. 134-144.
Carroll et al., "Clays and Clay Minerals", 1960, Proceedings of the Seventh Nat. Conf. on Clays & Clay Minerals, pp. 80, 90-99.
Stubican, "Clays and Clay Minerals", 1960, Proceedings of the Seventh Nat. Conf. on Clays & Clay Minerals, p. 295.
Barrer et al., "J. Chem. Soc.", 1961, pp. 983-990.
Barrer et al., "J. Chem. Soc.", 1964, pp. 2296-2305.

*Primary Examiner*—Edward J. Meros
*Attorney, Agent, or Firm*—Roy J. Ott

[57] ABSTRACT

A synthetic halloysite which is substantially iron-free is obtained by crystallization from a reaction mixture containing hydrous alumina gel and aqueous silica sol. Metal substituted synthetic halloysites can be prepared by coprecipitation of metal hydroxides with the alumina gel.

5 Claims, No Drawings

SYNTHETIC HALLOYSITES

BACKGROUND OF THE INVENTION

1. Field of the Invention

This invention relates to a novel composition of matter useful as a catalyst and/or catalyst base in hydrocarbon conversion reactions. More particularly, this invention relates to synthetic halloysite, its preparation and its use in hydrocarbon conversion reactions such as cracking, hydrocracking, hydrofining, desulfurization, and demetallization.

2. Description of the Prior Art

Halloysite is a well-known kaolin clay mineral having the empirical formula $Al_2O_3:2SiO_2:2H_2O$. A complete chemical analysis for halloysite is given in the "Encyclopedia of Chemical Technology," 2nd Edition, Vol. 5, page 545 (Interscience Publishers). Further descriptions concerning the properties and characteristics of naturally-occurring halloysite may be found in the literature such as, for example, Thomas F. Bates et al. (1950), Morphology and Structure of Endellite and Halloysite, The American Mineralogist, Vol. 35, pages 463–484; Thomas F. Bates et al., Further Observations on the Morphology of Chrysotile and Halloysite, Proceedings National Conference on Clays and Clay Minerals, VI, Berkeley, 1957 pages 237–248; and G. Brown, The X-Ray Identification and Crystal Structures of Clay Minerals, Mineralogical Society (Clay Minerals Group), London, 1961, pages 68–77.

Natural halloysite has been used heretofore in the petroleum art as a catalytic cracking catalyst. Unfortunately, naturally-occurring halloysite contains various metals, such as iron, which are detrimental to its effectiveness as a hydrocarbon conversion catalyst. It has been found, therefore, necessary to subject the naturally occurring halloysite to acid treatment in order to reduce the iron content and thereby increase its effectiveness as a hydrocarbon conversion catalyst. Unfortunately, acid treatment often does substantial damage to the crystalline structure of the halloysite which drastically limits its use as a catalyst in hydrocarbon conversion processes.

SUMMARY OF THE INVENTION

In accordance with the present invention, a synthetic halloysite which is substantially iron-free is obtained by crystallization from a reaction mixture containing hydrous alumina gel and aqueous silica sol. In a further embodiment of the invention, metal substituted synthetic halloysites are prepared by coprecipitation of metal hydroxides with the alumina gel.

In general, the halloysite of the invention is prepared by crystallization from an aqueous mixture containing a mixture of alumina gel and a silica source maintained at a pH of 4 to 10 for at least about 16 hours at a temperature in excess of 200° C. A preferred reaction scheme is given by the following equations:

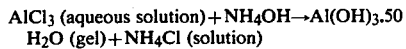

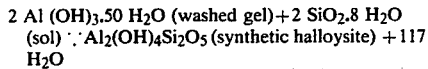

Metal substituted synthetic halloysites can be prepared in accordance with the invention by coprecipitation of a hydroxide of the metal with the alumina gel. The empirical formula for such metal substituted synthetic halloysites, which may have an $SiO_2/Al_2O_3$ ratio greater than the stoichiometric amount, can be expressed by the following formula:

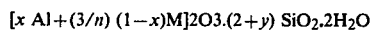

where
M is a metal selected from Groups IIA, IIIB, VIB and VIII of the Periodic Table
n is valence of M
x=0 to 1, preferably 0.8 to 1.0
y=0 to 1.

Preparation of the synthetic halloysite of the Invention involves the reaction of hydrous alumina gel, i.e., $Al(OH)_3$, and a source of silica. The hydrous alumina gel is prepared in accordance with known techniques such as by the reaction of aqueous mixtures of aluminum chloride or aluminum sulfate and an inorganic base such as $NH_4OH$, $NaOH$ or $NaAlO_2$, and the like. Preparation of alumina gel by use of ammonium hydroxide is preferable to the use of sodium hydroxide since it is desirable to maintain the soda ($Na_2O$) content to a low level and because the more alkaline gels tend to form crystalline boehmite.

The silica source may include those sources which are conventionally used for the preparation of crystalline aluminosilicate zeolites. These include silicic acid, silica sol, silica gel, sodium silicate, etc. Silica sols are particularly useful. These are colloidal dispersions of discrete spherical particles of surface-hydroxylated silica such as is sold by E. I. du Pont de Nemours & Company, Inc. under the trademark "Ludox."

The proportions of the reactants employed in the initial reaction mixture are determined from the following molar ratio of reactants.

| | Reactant Molar Ratio | | |
|---|---|---|---|
| | General | Preferred | Particularly Preferred |
| $Al(OH)_3/SiO_2$ | 0.5–1.2 | 0.8–1.0 | 0.9–1.0 |
| $H_2O/SiO_2$ | 20–60 | 30–50 | 40–50 |

The pH of the reaction mixture should be adjusted to a range of about 4 to 10, preferably 6 to 8. The temperature of the reaction mixture should preferably be maintained at between about 230° and 270° C., more preferably 240° to 250° C., for a period from about 2 hours to 100 hours or more. The time necessary for crystallization will depend, of course, upon the temperature of the reaction mixture. By way of example, the crystallization of the synthetic halloysite occurs in about 24 hours at a temperature of about 250° C.

The catalytic activity of the synthetic halloysites of the invention can be improved by incorporating therein metals selected from Groups IIA, IIIB, VIB, and VIII of the Periodic Table as given in "Websters Seventh New Collegiate Dictionary," (1963) published by G. C. Merriam Company. Specific examples of such metals include, among others, magnesium, lanthanum, molybdenum, cobalt, nickel, palladium, platinum and rare earths. Particularly preferred metals include magnesium, nickel, cobalt and lanthanum. The metals are incorporated into the synthetic halloysite structure by adding soluble salts of the metal to the reaction mixture or by coprecipitation of the metal hydroxide with $Al(OH)_3$. The metals are most conveniently added to the reaction mixture in the form of their hydroxides. The synthetic halloysite of the invention, particularly when substituted with the afore-described metals, is useful for catalytic cracking, hydrocracking, desulfurization, demetallization and other hydrocarbon conversion processes. For example, substituted halloysites of the invention containing metals such as magnesium, lanthanum and rare earths such as cerium, praseodymium, neodymium, gadolinium, etc., are useful in catalytic cracking of petroleum feedstocks. Synthetic halloysite containing nickel, cobalt, palladium, platinum, and the like are particularly useful for hydrocracking petroleum feedstocks.

The feedstocks suitable for conversion in accordance with the invention include any of the well-known feeds conventionally employed in hydrocarbon conversion processes. Usually they will be petroleum derived, although other sources such as shale oil are not to be excluded. Typical of such feeds are heavy and light virgin gas oils, heavy and light virgin naphthas, solvent extracted gas oils, coker gas oils, steam-cracked gas oils, middle distillates, steam-cracked naphthas, coker naphthas, cycle oils, deasphalted residua, etc.

The operating conditions to be employed in the practice of the present invention are well-known and will, of course, vary with the particular conversion reaction desired. The following table summarizes typical reaction conditions effective in the present invention.

sites also differ in that the physical form of the synthetic halloysite is flakes, while the physical form of the natural halloysite has a tube-like configuration. Furthermore, it has been discovered that the synthetic halloysite has considerably better catalytic activity than natural halloysite under analogous hydrocarbon conversion conditions. Although the synthetic halloysite has the same empirical formula as naturally occurring halloysite, the higher surface area, the elimination of iron and the presence of selective metals makes the synthetic halloysite a more effective hydrocarbon conversion catalyst.

DESCRIPTION OF THE PREFERRED EMBODIMENTS

The following examples further illustrate the present invention. Unless otherwise specified, all percentages and parts are by weight.

EXAMPLE 1

This example illustrates a general procedure for the preparation of the synthetic halloysite of the invention.

A solution consisting of 962 grams of $AlCl_3 \cdot 6H_2O$ in 3,200 cubic centimeters (cc) of water were added to a 1 gallon stainless steel vessel. The solution was stirred at ambient conditions and neutralized with about 740 cc. of a 28% ammonia solution, thereby producing a pH greater than 8. The $Al(OH)_3$ gel produced was washed

| | Reaction Conditions | | | |
|---|---|---|---|---|
| Principal Conversion Desired | Temperature, °F. | Pressure, p.s.i.g. | Feed Rate V/V/Hr. | Hydrogen Rate s.c.f./bbl. |
| Hydrofining | 500–800 | 50–2,000 | 0.1–10.0 | 500–10,000 |
| Hydrocracking | 450–850 | 200–2,000 | 0.1–10.0 | 500–10,000 |
| Catalytic Cracking | 700–1,000 | 0–50 | 0.1–20.0 | 0 |
| Catalytic Reforming | 850–1,000 | 50–1,000 | 0.1–20.0 | 500–10,000 |

The halloysite structure of the composition of this invention has been confirmed by X-ray diffraction and electron microscopy. However, there are a number of significant differences between naturally occurring halloysite and the synthetic halloysite of this invention. For example, the synthetic halloysites of the invention have surface areas ranging from about 85 sq. meters/gram to about 200 sq. meters/gram (BET Method as used, for example, in U.S. Pat. No. 3,804,741) as compared to naturally occurring halloysite which has a surface area generally within the range of 40–85 sq. meters/gram (BET Method). Further, the synthetic halloysite of the invention will be substantially iron-free, i.e., less than 0.05% iron, as compared to naturally occurring halloysite which contains significant amounts of iron. The synthetic and naturally occurring halloywith water until it was substantially chloride-free. The washed $Al(OH)_3$ gel was then blended with 790 grams of silica sol sold under the trade name "LS-30 Ludox" by E. I. du Pont de Nemours & Company. The blend of silica sol and alumina gel was then transferred to a 200 cc. Monel autoclave where it was heated at 246° C. for 48 hours to produce synthetic halloysite.

EXAMPLE 2

Using the general procedure of Example 1, a number of synthetic halloysites were prepared to determine the surface area of synthetic halloysite prepared in accordance with the invention. The results given below in Table I show that the surface area expressed in square meters per gram is higher than naturally occurring halloysite.

TABLE I

| SURFACE AREA OF SYNTHETIC HALLOYSITE | | | | | | |
|---|---|---|---|---|---|---|
| Gel Composition | | | | Crystallization | | |
| Silica Source | Al Source | Al/Si | $H_2O/Al_2O_3$ | Conditions | Surface Area[1] | ($m^2/g$, BET Method) |
| LS-30 Ludox[2] | $Al(OH)_3$[3] | 1.0 | 72 | 20 Hr. at 250° C. | 114 | |
| LS-30 Ludox | $Al(OH)_3$ | 1.0 | 89 | 20 Hr. at 246° C. | 88 | |
| LS-30 Ludox | $Al(OH)_3 + MgCl_2$ | 0.9 | 100 | 20 Hr. at 246° C. | 103 | |
| LS-30 Ludox | $Al(OH)_3 + NiCl_2$ | 0.9 | 100 | 20 Hr. at 246° C. | 118 | |
| LS-30 Ludox | $Al(OH)_3 + FeCl_2$ | 0.9 | 100 | 20 Hr. at 246° C. | 91 | |
| LS-30 Ludox | $Al(OH)_3 + CoCl_2$ | 0.9 | 100 | 20 Hr. at 246° C. | 93 | |
| LS-30 Ludox | $Al(OH)_3$ | 1.0 | 86 | 48 Hr. at 246° C. | 99 | |
| LS-30 Ludox | $Al(OH)_3 + Mg(OH)_2$ | 1.0 | 67 | 48 Hr. at 255° C. | 193 | |

TABLE I-continued

SURFACE AREA OF SYNTHETIC HALLOYSITE

| | Gel Composition | | | Crystallization | |
|---|---|---|---|---|---|
| Silica Source | Al Source | Al/Si | $H_2O/Al_2O_3$ | Conditions | Surface Area[1] (m.$^2$/g, BET Method) |
| LS-30 Ludox | $Al(OH)_3 + Mg(OH)_2$ | 1.0 | 67 | 48 Hr. at 246° C. | 143 |

[1]Naturally occurring halloysite typically has a surface area in the range of 45-85 m.$^2$/g.
[2]Colloidal silica sol (150 A.) particle size sold by E. I. du Pont de Nemours & Company.
[3]$AlCl_3$ neutralized with NaOH and washed.

EXAMPLE 3

Using the general preparation procedure given in Example 1, a number of metal-substituted synthetic halloysites were prepared by precipitating insoluble hydroxides of various metals with aluminum hydroxide and blending the resultant washed gel with the silica sol. The reaction conditions and the amount of substituted metal in the synthetic halloysite product are given in Table II.

TABLE II

| Experiment* | Synthesis Gel, Molar Proportions | $H_2O/Al_2O_3$ Mole Ratio | Product Yield** | Amount of Substituted Metal in Product, Wt. % |
|---|---|---|---|---|
| A | $SiO_2$ Sol + $Al(OH)_3$ + 0.15 $Mg(OH)_2$ | 72 | 81 | 1.23% Mg |
| B | $SiO_2$ Sol + $Al(OH)_3$ + 0.15 $Ni(OH)_2$ | 66 | 71 | 2.6% Ni |
| C | $SiO_2$ Sol + $Al(OH)_3$ + 0.15 $Fe(OH)_2$ | 77 | 94 | 4.6% Fe |
| D | $SiO_2$ Sol + $Al(OH)_3$ + 0.15 $Co(OH)_2$ | 84 | 82 | 5.6% Co |

*In all experiments, the Al/Si mole ratio in reaction mixture was 0.94 and crystallization conditions were 24 hours at 246° C.
**Wt. % of theoretical yield calculated as $Al_2O_3.2SiO_2.2H_2O$.

EXAMPLE 4

The catalysts prepared in the previous example were pressed on a hydraulic ram, the compacted forms of the catalyst then crushed to 14-35 mesh (Tyler series), and then calcined at 540° C. for 16 hours. Portions of this granular catalyst were charged to reactors and the temperature adjusted to 280° C. A stream of helium was passed through a saturator filled with cumene at 18° C. and passed into the reactor and contacted with the catalyst. The effluent from the reactor was analyzed by gas chromatography to determine the amount of conversion of the cumene to benzene and propylene. The results obtained were compared with natural halloysite (API Standard No. 13). The results obtained were given below in Table III.

cantly improved by substituting such metals as magnesium and nickel in the structure. Conversely, the incorporation of iron in synthetic halloysites acts as a catalyst poison, just as it does in natural halloysites.

EXAMPLE 5

This example compares in Table VI the X-ray powder diffraction pattern of a typical synthetic halloysite of the invention with the published patterns for naturally occurring halloysite (ASTM 13-375) and the closely related mineral kaolinite (ASTM 14-164).

In obtaining the X-ray powder diffraction pattern, standard procedures were employed. The radiation source was the K-alpha doublet for copper. A Geiger counter spectrometer with a strip chart pen recorder was used in recording the data. The peak heights I, and the positions as a function of $2\theta$, where $\theta$ is the Bragg angle, were read from the spectrometer chart. From these, the relative intensities I were observed. Also, the interplanar spacing, d, in Angstrom units, corresponding to the recorded lines, were determined by reference to standard tables. The more significant interplanar spacings, i.e., d values, for a typical synthetic halloysite of the invention, natural halloysite and kaolinite are shown below in Table IV. As regards the synthetic halloysite of the invention, the relative intensities of the lines are expressed as s. (strong), m. (medium) and w. (weak).

TABLE III

CUMENE CRACKING ACTIVITY

| Catalyst Description | W/Hr./W (G. of Cumene/Hr./G. of Cat.) | Cumene Conversion, % (At 525° F. After 30 Minutes) | K*(Hr.$^{-1}$) |
|---|---|---|---|
| Natural Halloysite (API #13) | 0.08 | 8 | 0.006 |
| Syn. Halloysite of Example 1 | 0.08 | 16 | 0.013 |
| Mg-Substituted Syn. Halloysite Product A of Example 3 | 0.075 | 60 | 0.068 |
| Ni-Substituted Syn. Halloysite Product B of Example 3 | 0.081 | 37 | 0.038 |
| Fe-Substituted Syn. Halloysite Product C of Example 3 | 0.22 | 0 | 0 |
| Syn. Halloysite of Example 1 | 0.22 | 5 | 0.012 |
| Co-Substituted Syn. Halloysite Product D of Example 3 | 0.22 | 10 | 0.023 |
| Mg-Substituted Syn. Halloysite Product A of Example 3 | 0.22 | 43 | 0.124 |
| Ni-Substituted Syn. Halloysite Product B of Example 3 | 0.22 | 25 | 0.062 |
| Mg-Substituted Syn. Halloysite Product A of Example 3 | 0.26 | 18 | 0.052 |

*First order rate constant for cumene cracking reaction.

The above data show the effectiveness of the synthetic halloysites of the invention as cracking catalyst. Synthetic halloysite is more active than natural halloysite and the activity of synthetic halloysite is signifi-

TABLE IV

X-RAY DIFFRACTION PATTERNS FOR HALLOYSITES AND KAOLINITE

| Synthetic Halloysite* | | | Natural Halloysite** | | | Kaolinite*** | | |
|---|---|---|---|---|---|---|---|---|
| d(A) | I | hkl | d(A) | $I/I_1$ | hkl | d(A) | $I/I_1$ | hkl |
| 7.3 | m. | 001 | 7.4 | 95 | 001 | 7.17 | 100 | 001 |
| 4.43 | s. | 11.02 | 4.41 | 100 | 11.02 | 4.48 | 35 | 020 |
| 3.56 | m. | 002 | 3.62 | 65 | 002 | 4.37 | 60 | 110 |
| 2.55 | m. | 20.13 | 2.58 | 30 | 20.13 | 3.58 | 80 | 002 |
| 2.34 | m. | 003 | 2.39, 2.32 | 35 | 003 | 2.385 | 25 | 003 |
| 1.68 | m. | 24.31 | 1.70, 1.67 | 20 | 26.31 | 1.94 | 35 | 132 |
| 1.49 | m. | 33.06 | | | | | | |

*First-listed product of Table I
**ASTM 13-375
***ASTM 14-164

As regards synthetic halloysite and the related kaolinite mineral, the d line at 4.43 Å is significant. Kaolinite has d lines at 4.48 Å and 4.37 Å, but no strong intensity d line at 4.43 Å as in the case of the synthetic halloysite of the invention. The synthetic halloysite of the invention can also be distinguished on the basis that the d line at 4.43 Å is of stronger intensity than either the 001 line (d=7.3) or the 002 (d=3.56). Accordingly, the significant X-ray diffraction characteristics of the synthetic halloysite of the invention are as follows:

| d(Å) | I |
|---|---|
| 7.3±0.2 | m |
| 4.42±0.02 | s |
| 3.56±0.04 | m |

What is claimed is:

1. A process for preparing halloysite which comprises forming a reaction mixture of aluminum hydroxide gel, silica sol and water having a $Al(OH)_3/SiO_2$ molar ratio in the range of 0.5 to 1.2 and a $H_2O/SiO_2$ molar ratio in the range of 20 to 60 and maintaining said reaction mixture at a pH in the range of 4 to 10 and a temperature of about between 230° and 270° C. for a time sufficient to permit crystallization of halloysite.

2. The process of claim 1 wherein said aluminum hydroxide gel is prepared from the reaction of hydrous aluminum chloride and ammonia.

3. The process of claim 1 wherein said $Al(OH)_3/SiO_2$ molar ratio is in the range of 0.8 to 1.0 and said $H_2O/SiO_2$ molar ratio is in the range of 30 to 50.

4. The process of claim 3 where said pH is in the range of 6 to 8.

5. The process of claim 4 wherein said $Al(OH)_3/SiO_2$ molar ratio is in the range of 0.9 to 1.0 and said $H_2O/SiO_2$ molar ratio is in the range of 40 to 50.